(12) United States Patent
Yu et al.

(10) Patent No.: US 10,796,551 B2
(45) Date of Patent: Oct. 6, 2020

(54) WEARABLE DEVICE AND MONITORING SYSTEM COMPRISING SAME

(71) Applicant: Robert Bosch GmbH, Stuttgart (DE)

(72) Inventors: Huajun Yu, Shanghai (CN); MingLiang Zhang, Shanghai (CN); Patrick Poa, Shanghai (CN); Wei Wang, Shanghai (CN)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 16/336,583

(22) PCT Filed: Oct. 3, 2016

(86) PCT No.: PCT/CN2016/101424
§ 371 (c)(1),
(2) Date: Mar. 26, 2019

(87) PCT Pub. No.: WO2018/064792
PCT Pub. Date: Apr. 12, 2018

(65) Prior Publication Data
US 2019/0221100 A1    Jul. 18, 2019

(51) Int. Cl.
*G08B 21/04* (2006.01)
*F16P 3/14* (2006.01)
*A61B 5/00* (2006.01)
*G06T 7/20* (2017.01)

(52) U.S. Cl.
CPC ........ *G08B 21/0446* (2013.01); *A61B 5/6804* (2013.01); *F16P 3/147* (2013.01); *G06T 7/20* (2013.01)

(58) Field of Classification Search
CPC .......... A61B 5/6804; F16P 3/147; G06T 7/20; G08B 21/0446
See application file for complete search history.

(56) References Cited

FOREIGN PATENT DOCUMENTS

| CN | 201392588 Y | 1/2010 |
|---|---|---|
| CN | 201600501 | 10/2010 |
| CN | 201600501 U | * 10/2010 |
| CN | 104076380 | 10/2014 |
| CN | 104346902 A | 2/2015 |
| CN | 104661308 | 5/2015 |

(Continued)

OTHER PUBLICATIONS

International Search Report for Application No. PCT/CN2016/101424 dated Jun. 22, 2017 (English Translation, 3 pages).

*Primary Examiner* — Omeed Alizada
(74) *Attorney, Agent, or Firm* — Michael Best & Friedrich LLP (57) ABSTRACT

The present invention provides a wearable device, comprising: a power source; a position sensor electrically connected to the power source, for sensing a position of a wearer of the wearable device and generating a position signal; a signal transceiver electrically connected to the power source, for receiving the position signal, sending the position signal to a monitoring apparatus, and receiving an indication signal from the monitoring apparatus; and a body of the wearable device comprises a first part and a second part, wherein a relative position of a moveable end of the first part and a moveable end of the second part can switch between a first relative position and a second relative position.

16 Claims, 3 Drawing Sheets

(56) References Cited

FOREIGN PATENT DOCUMENTS

| | | | |
|---|---|---|---|
| CN | 104954981 | A | 9/2015 |
| CN | 105160807 | | 12/2015 |
| CN | 105160807 | A * | 12/2015 |
| CN | 205123722 | U | 3/2016 |
| CN | 105872952 | | 8/2016 |
| EP | 2698972 | A1 | 2/2014 |
| FR | 1349789 | A | 1/1964 |
| JP | 3771892 | | 4/2006 |
| WO | 0182259 | | 11/2001 |
| WO | 2014015527 | A1 | 1/2014 |
| WO | 2014101046 | A1 | 7/2014 |

* cited by examiner

WEARABLE DEVICE AND MONITORING SYSTEM COMPRISING SAME

BACKGROUND OF THE INVENTION

The present invention relates to monitoring technology, more specifically to a wearable device which can be used in a monitored site.

In an environment containing high-speed industrial robots or dangerous equipment, to avoid accidents, certain measures are generally adopted to protect staff entering the environment.

A common approach is to install a warning sign in a region comprising high-speed industrial robots or dangerous equipment. A better approach is to install not only a warning sign but also a protective fence, etc. In some places, special attendants are provided, for the purpose of preventing unauthorized staff from entering or reminding operators to take care, etc.

In the case of staff who disregard protective measures such as warnings or perimeter fences and enter by force, the abovementioned methods of prevention are useless.

SUMMARY OF THE INVENTION

In view of the above, the present invention provides a wearable device, to be worn by staff entering a site to be monitored, so as to facilitate monitoring.

The wearable device comprises: a power source; a position sensor electrically connected to the power source, for sensing a position of a wearer of the wearable device and generating a position signal; a signal transceiver electrically connected to the power source, for receiving the position signal, sending the position signal to a monitoring apparatus, and receiving an indication signal from the monitoring apparatus; and a body of the wearable device comprises a first part and a second part, wherein a relative position of a moveable end of the first part and a moveable end of the second part can switch between a first relative position and a second relative position.

In the wearable device according to the present invention, optionally, the switching of the relative position between the first relative position and the second relative position can turn the power source on or off.

In the wearable device according to the present invention, optionally, the position sensor comprises a first position sensor and a second position sensor, the signal transceiver comprises a first signal transceiver and a second signal transceiver, the first position sensor and the first signal transceiver being disposed at the first part, and the second position sensor and the second signal transceiver being disposed at the second part.

In the wearable device according to the present invention, as an example, the power source is disposed on a power source carrier, the first part being pivot-connected by means of a non-moveable end thereof to one end of the power source carrier, and the second part being pivot-connected by means of a non-moveable end thereof to another end of the power source carrier.

In the wearable device according to the present invention, optionally, the switching of position of the moveable end of the first part between the first relative position and the second relative position can cause the power source to supply power or stop supplying power to the first signal transceiver and the first position sensor, and the switching of position of the moveable end of the second part between the first relative position and the second relative position can cause the power source to supply power or stop supplying power to the second signal transceiver and the second position sensor.

Optionally, the wearable device according to the present invention further comprises an indication module, set to make a corresponding indication when the signal transceiver receives an indication signal from the monitoring apparatus. For example, if the indication signal indicates that the wearer is located in a region requiring a warning, then the indication module issues e.g. a yellow light to show a reminder; if the indication signal indicates that the wearer is located in a highly dangerous region, then the indication module issues e.g. a red light to provide a reminder.

In the wearable device according to the present invention, a wearing region is any one of a neck, a wrist and a head.

According to one aspect of the present invention, a monitoring system is also provided, comprising a wearable device and a monitoring apparatus in communicative connection with each other, wherein the wearable device is any one of the wearable devices described above.

According to another aspect of the present invention, a monitoring method is also provided, comprising: providing a wearable device to an entering staff member, the wearable device being set to comprise a position sensor and a signal transceiver; the wearable device in an operational state sensing position information of the entering staff member, and transmitting a sensing signal indicating position information to a monitoring apparatus; the monitoring apparatus determining whether a position of the entering staff member is in a safe region, a region requiring a warning or a highly dangerous region on the basis of the sensing signal; the monitoring apparatus performing a corresponding operation on the basis of the determined region.

DETAILED DESCRIPTION

Schematic examples of the present invention are now described with reference to the accompanying drawings, in which identical reference labels represent identical elements. The examples described below will help those skilled in the art to thoroughly understand the present invention, and are intended to be demonstrative, not restrictive.

Figure 1:
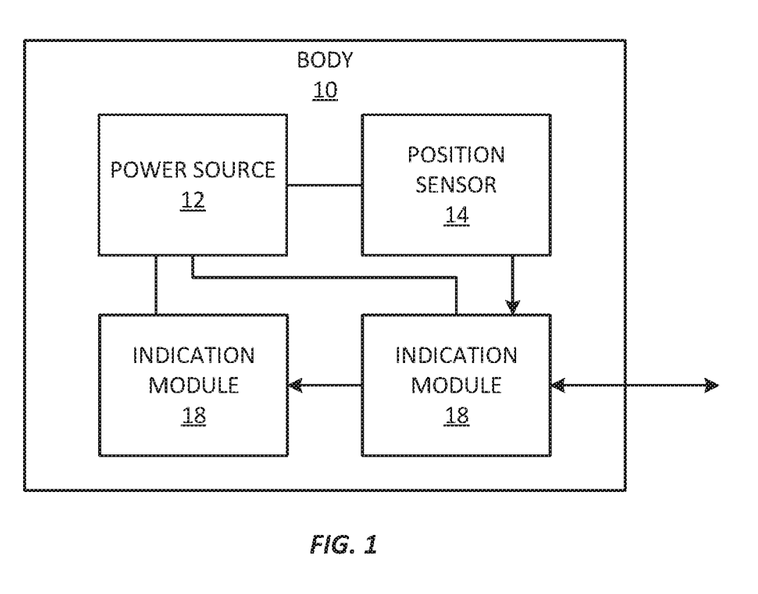
FIG. 1 is a structural schematic diagram of a wearable device according to an example of the present invention.

FIG. 1 is a structural schematic diagram of a wearable device according to an example of the present invention. The wearable device comprises a power source 12, a position sensor 14 and a signal transceiver 16. According to this example, the power source 12, position sensor 14 and signal transceiver 16 are all disposed on a body 10 of the wearable device. Here, disposing a component on the body 10 of the wearable device should be understood as meaning that the component is disposed on a surface of the body 10, or the component is disposed in the body 10, or a part of the component is disposed in the body 10 while another part can protrude from the body 10 or be outside the body 10, or the component is connected to the body 10 in a suitable manner.

Both the position sensor 14 and the signal transceiver 16 are electrically connected to the power source 12, wherein the power source 12, when turned on, supplies power to the position sensor 14 and the signal transceiver 16. The position sensor 14 is used to sense a position of a wearer wearing the wearable device, and generates a position signal.

The position sensor 14 is for example an ultra-wideband module, i.e. a UWB positioning module, and the UWB positioning module may be realized as a UWB positioning chip. The signal transceiver 16 and the position sensor 14 are electrically connected to each other. In some examples, they are realized in the same module or integrated together. The position signal generated by the position sensor 14 is sent out via the signal transceiver 16. According to an example of the present invention, the signal transceiver 16 sends the position signal to a monitoring apparatus. The signal transceiver 16 also receives an indication signal from the monitoring apparatus. In general, the indication signal indicates whether the wearer is in a region requiring a warning, a highly dangerous region or a safe region of a site entered by the wearer. For example, the signal transceiver 16 may be realized as an antenna.

Referring to FIG. 1, after putting on the wearable device, the wearer turns on the power source 12, such that the power source supplies power to the position sensor 14 and the signal transceiver 16. The position sensor 14 senses a position of the wearer, and transmits to the signal transceiver 16 a position signal generated on the basis of sensing; the signal transceiver 16 then transmits the position signal to the monitoring apparatus. The monitoring apparatus accordingly determines the position of the wearer and determines whether the wearer is in a region requiring a warning, a highly dangerous region or a safe region, and sends an indication signal to the wearable apparatus according to a determination result; the signal transceiver 16 receives the indication signal.

According to an example of the present invention, the body 10 of the wearable device comprises a first part and a second part, and a relative position of a moveable end of the first part and a moveable end of the second part can switch between a first relative position and a second relative position.

According to an example of the present invention, once the wearable device has been put on, the wearable device can be fixed to a wearing region by means of an action between the moveable end of the first part and the moveable end of the second part on the one hand and a wearing region on the other. For example, when the wearable device is a pair of spectacles, the pair of spectacles is fixed to a head through an action between an ear and a moveable end of one spectacles arm serving as the first part, and an action between another ear and a moveable end of another spectacles arm serving as the second part.

It must be explained that the expression "fixed to a wearing region" used here means that when worn, the wearable device will not fall off. Those skilled in the art should understand that when not needed, the wearable device can be taken off the body of the wearer. The first part and the second part are expounded further below with reference to the example of FIG. 2.

According to a schematic example of the present invention, the position sensor 14 comprises a first position sensor and a second position sensor; the signal transceiver 16 comprises a first signal transceiver and a second signal transceiver. The first position sensor and the second position sensor back up each other; the first signal transceiver and the second signal transceiver back up each other.

In some examples, a first switch and a second switch are provided for the power source 12. When the first switch is turned on, the first position sensor of the position sensor 14 and the first signal transceiver of the signal transceiver 16 operate; when the second switch is turned on, the second position sensor of the position sensor 14 and the second signal transceiver of the signal transceiver 16 operate. In this example, in the case where the second position sensor and the second transceiver serve as backup for the first position sensor and the first signal transceiver respectively, if either one of the first position sensor and the first transceiver develops a fault, the backup second position sensor and second signal transceiver are activated by turning on the second switch.

In other examples, a first switch, a second switch and a third switch are provided for the power source 12. When the first switch is turned on, the first position sensor of the position sensor 14 and the first signal transceiver of the signal transceiver 16 operate; when the second switch is turned on, the second position sensor of the position sensor 14 is supplied with power; when the third switch is turned on, the second signal transceiver of the signal transceiver 16 operates. In this example, in the case of a fault in the first position sensor, the second position sensor is activated by means of the second switch. In the case of a fault in the first signal transceiver, the second signal transceiver is activated by means of the third switch. In this example, the second position sensor is electrically connected to the first signal transceiver, and the second signal transceiver is electrically connected to the first position sensor.

In other examples, when the power source 12 is turned on, the first position sensor and the second position sensor simultaneously obtain a supply of power; sensed position signals are transmitted via the first signal transceiver and the second signal transceiver respectively, and received by the monitoring apparatus. In this example, the power source 12 may be turned on and off by a switch.

According to an example of the present invention, the wearable device shown in FIG. 1 further comprises an indication module 18. The indication module 18 is electrically connected to the signal transceiver 16. When the signal transceiver 16 receives an indication signal from the monitoring apparatus, indication is performed. The indication module may for example be an optical indication module (such as an LED lamp flash, etc.), a buzzer module, an audio indication module or any combination of these modules. The indication module 18 for example is used for indicating whether a position of the wearer is dangerous, the degree of danger, etc. For example, an optical indication module (if included) of the indication module 18 shows a green colour when the wearer is in a safe region, a yellow colour in a region requiring a warning, and a red colour in a highly dangerous region; in a highly dangerous region, an indication may be made jointly by an optical indication module and an audio indication module or buzzer module (if present) at the same time.

Figure 2:
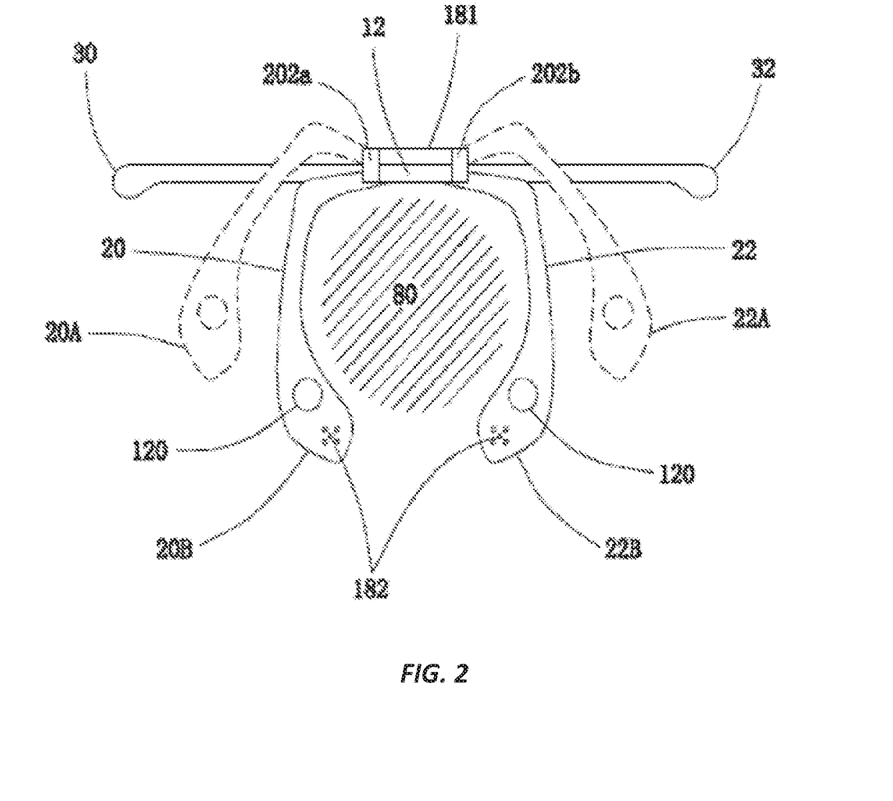
FIG. 2 is a demonstrative structure of a wearable device according to the present invention.

FIG. 2 is a demonstrative structure of a wearable device according to the present invention. In the example shown in FIG. 2, the wearable device is intended to be worn on a neck 80 of the wearer. In this example, the wearable device comprises a first part 20 and a second part 22. A moveable end of the first part 20 can move between a position 20A and a position 20B; a moveable end of the second part 22 can move between a position 22A and a position 22B. When the moveable end of the first part 20 is at position 20A and the moveable end of the second part 22 is at position 22A, this constitutes a first relative position of the moveable end of the first part 20 and the moveable end of the second part 22. When the moveable end of the first part 20 is at position 20B and the moveable end of the second part 22 is at position 22B, this constitutes a second relative position of the moveable end of the first part 20 and the moveable end of the second part 22.

The movement of the moveable end of the first part 20 from position 20A to position 20B and the moveable end of the second part 22 from position 22A to position 22B, i.e. the movement of the two moveable ends from the first relative position to the second relative position, causes the wearable device to be worn on the neck 80 of the wearer.

In the example of FIG. 2, a signal transceiver is realized as an antenna, and in this example, the antenna and a position sensor are realized in the same module. Referring to FIG. 2, a first position sensor and a first signal transceiver (also called a first antenna hereinbelow) are realized in a first module 30; a second position sensor and a second signal transceiver (also called a second antenna hereinbelow) are realized in a second module 32. The first module 30 is disposed at the first part 20; the second module 32 is disposed at the second part 22. In the example shown in FIG. 2, the first module 30 is fixed to the first part 20 but extends from the first part 20; the second module 32 is fixed to the second part 22 but extends from the second part 22. Alternatively, the first module 30 may be disposed in approximately the middle of the first part 20; the second module 32 may be disposed in approximately the middle of the second part 22. It must be explained that the arrangement of the first module 30 and the second module 32 is not limited to that shown in the present invention; they can be arranged in suitable positions of the first part 20 and the second part 22 according to actual needs.

Referring to FIG. 2, in this example, a power source 12 is disposed on a power source carrier (not marked); a non-moveable end (not marked) of the first part 20 is pivot-connected to the power source carrier, and a non-moveable end (not marked) of the second part 22 is pivot-connected to the power source carrier. In this example, when the moveable end of the first part 20 and the moveable end of the second part 22 switch from the first relative position (position 20A and position 22A) to the second relative position (position 20B and position 22B), the power source 12 is turned on, and thereby supplies power to the first module 30 and the second module 32. Conversely, when the moveable end of the first part 20 and the moveable end of the second part 22 switch from the second relative position to the first relative position, the power source 12 is turned off, and stops supplying power to the first module 30 and the second module 32.

In one very specific example, in FIG. 2, a first switch 202*a* and a second switch 202*b* may be provided. The turning-on of the first switch 202*a* is achieved when the first part 20 switches from position 20A to position 20B, and the turning-on of the second switch 202*b* is achieved when the second part 22 switches from position 22A to position 22B. Conversely, the first switch 202*a* is turned off when the first part 20 switches from position 20B to position 20A, and the second switch 202*b* is turned off when the second part 22 switches from position 22B to position 22A. As an alternative to this specific example, the turning-on and turning-off of the power source 12 may be controlled by just one switch; the "off" and "on" actions of the switch are achieved through the switching of the relative position between the first relative position and the second relative position. For example, when the relative position is the first relative position, the switch is in an OFF state, and when the relative position is the second relative position, the switch is in an ON state.

According to an example of the present invention, the wearable device may further comprise an optical warning module, such as an LED lamp, to issue indication signals by displaying different colours; for example, when a red colour is displayed, this indicates a high level of danger, a yellow colour indicates a warning, and a green colour indicates safety. If necessary, the optical warning module may be formed as a lamp flash. In the schematic example of FIG. 2, an optical warning module 181 is disposed on the power source carrier. For example, when an indication signal received by the signal transceiver from a monitoring apparatus indicates that the wearer is in a safe region, the optical warning module 181 shows a green colour; when an indication signal received by the signal transceiver from the monitoring apparatus indicates that the wearer is in a region requiring a warning, the optical warning module 181 shows a yellow colour; when an indication signal received by the signal transceiver from the monitoring apparatus indicates that the wearer is in a highly dangerous region, the optical warning module 181 shows a red colour.

In the example of FIG. 2, the wearable device further comprises an indication module disposed at the first part 20 and/or the second part 22, the indication module being used for indicating a charge level of the power source 12, and for example being disposed at an end of the first part and/or the second part 22. Optionally, an audio indication module 182 is disposed at the first part 20 and/or the second part 22 of the wearable device, such that a warning signal etc. can be issued in voice form. For example, a buzzer module may also be provided. In the specific example shown in FIG. 2, indication modules 120 for indicating the charge level of the power source 12 and audio indication modules 182 are disposed at each of the moveable ends of the first part 20 and the second part 22.

Furthermore, as an alternative, in FIG. 2, the indication module for indicating the charge level of the power source 12 may be disposed directly in the vicinity of a battery, or in the case where the wearable device comprises a carrier carrying a battery, disposed on the battery carrier, or if possible, disposed directly on a battery casing, etc. Similarly, the audio indication module may also be disposed in another position of the body as required.

According to some embodiments of the present invention, in the wearable device, the power source 12 may be disposed on the first part 20 or the second part 22. The power source 12 supplies power to the first module 30 when the first switch is turned on; the power source 12 supplies power to the second module 32 when the second switch is turned on. For example but without restriction, the turning-on of the first switch and the second switch may be achieved by a button, operated manually by the wearer.

According to other examples of the present invention, in the wearable device, the first part 20 and the second part 22 are pivot-connected by means of the non-moveable ends thereof. The power source 12 is disposed at a pivot connection position of the first part 20 and the second part 22; specifically, the first switch is disposed in a place close to the first part 20 at the pivot connection position, and the second switch is disposed in a place close to the second part 22 at the pivot connection position. Similarly to the example shown in FIG. 2, in this example, the turning-on of the first switch is achieved when the first part 20 switches from position 20A to position 20B, and the turning-on of the second switch is achieved when the second part 22 switches from position 22A to position 22B. Conversely, the first switch is turned off when the first part 20 switches from position 20B to position 20A, and the second switch is turned off when the second part 22 switches from position 22B to position 22A.

According to some examples of the present invention, an alarm button may also be disposed on the body of the wearable device; the alarm button is connected to the power source 12 to obtain power. Optionally, the alarm button is electrically connected to the signal transceiver, so that an alarm signal can be transmitted to the monitoring apparatus by the signal transceiver. Optionally, the alarm button is electrically connected to the audio indication module, so that an alarm signal can issue an audio indication via the audio indication module. The alarm button helps the wearer to issue a distress signal in an emergency or a dangerous situation.

In all of the examples described above, each module and component is supplied with power by the power source 12. For example, the first module 30, the audio indication module disposed at the end of the first part 20, and the indication module indicating the charge level of the power source 12, etc. are all supplied with power by the power source 12 via the first switch when turned on; correspondingly, the second module 32, the audio indication module disposed at the end of the second part 22, and the indication module indicating the charge level of the power source 12, etc. are all supplied with power by the power source 12 via the second switch when turned on. The optical warning module may be set to be supplied with power when the power source 12 is turned on by the first switch or the second switch.

As an alternative, according to each example of the present invention, the power source 12 may comprise a first power source and a second power source. The first power source supplies power to the first position sensor and the first signal transceiver; the second power source supplies power to the second position sensor and the second signal transceiver. Furthermore, in the case where the first part and the second part are each provided with a charge level indication module and an audio indication module, the first power source may supply power to the charge level indication module and audio indication module disposed on the first part, and the second power source may supply power to the charge level indication module and audio indication module disposed on the second part. For example, the first power source supplies power to a first position sensor, a first signal transceiver, a first charge level indication module and an audio indication module disposed on the first part, and the first power source may be controlled by means of a first switch provided therefor. The first switch may control turning on/off by means of a button, or may control turning on/off by means of a change in position of the moveable end of the first part as referred to above. The second power source supplies power to a second position sensor, a second signal transceiver, a second charge level indication module and an audio indication module disposed on the second part. The second switch may control turning on/off by means of a button, or may control turning on/off by means of a change in position of the moveable end of the second part as referred to above. In this example, positions in which the first power source and the second power source are disposed may be as in the examples described above: disposed on a power source carrier, or disposed in suitable positions of the first part and the second part respectively, or disposed at a pivot connection position of the first part and the second part, etc.

In this example, if one of the first power source and the second power source has insufficient power, the other power source can still supply power to the position sensor and the signal transceiver which are electrically connected thereto, so that they can still be in an operational state.

For example, when a staff member wishes to enter a site containing electromechanical equipment/robots etc. operating at high speed or other equipment posing a certain danger to entering staff, the staff member may be asked to wear a wearable device according to an example of the present invention, e.g. the wearable device shown in FIG. 2. The entering staff member wearing the wearable device operates the first part 20 and the second part 22 to change the positions of the moveable ends thereof, then turns on the power source at the same time as fixing the device to the wearer's neck; the first module, second module and other modules of the wearable device are supplied with power by the power source 12 which has been turned on, thereby entering an operational state. The first module 30 and the second module 32 sense a movement position of the wearer in the site, and send sensing signals to a monitoring apparatus by wireless transmission; the monitoring apparatus is for example disposed in a monitoring room. Parameters associated with a dangerous region have already been preset for the site in the monitoring apparatus, e.g. a setting has already been performed regarding which region is a safe region, which region is a region requiring a warning, and which region is a highly dangerous region, etc., wherein regions can be set by means of transverse and longitudinal position parameters. After receiving the sensing signals from the first module and the second module 30 and 32, the monitoring apparatus determines the position of the wearer. If the wearer is in a safe region, the monitoring apparatus sends a safe signal to the wearable device; at this time, the optical indication module of the wearable device shows a green colour. Alternatively, the monitoring apparatus may also be set to not send a signal when the wearer is in a safe region, and the optical indication module is set to show a green colour in this case. When the wearer is in a region requiring a warning, the monitoring apparatus sends a corresponding warning signal to the wearable device; the signal transceivers disposed in the first and second modules receive the warning signal and transmit the warning signal to the optical indication module, which shows a yellow colour accordingly. When the wearer is in a highly dangerous region, a warning signal indicating presence in a highly dangerous region is sent to the wearable device; the signal transceivers disposed in the first and second modules receive the signal and transmit the signal to the optical indication module, which shows a red colour accordingly. In this example, when a warning signal for presence in a highly dangerous region is received, the signal transceivers simultaneously send the signal to the audio indication modules, so that they issue a warning in audio form that the wearer is in a dangerous region. When either one of the first module 30 and the second module 32 develops a fault, the transmission of the wearer's position to the monitoring apparatus and the receiving of an indication signal from the monitoring apparatus by the wearable device are not affected, because the other one of the first and second modules is still operational.

If the wearer is wearing a wearable device having a first power source and a second power source as mentioned above, then even if one of the power sources has no power or has a fault, the other power source can still supply power to corresponding components and modules so that the wearable device is in an operational state.

Figure 3:
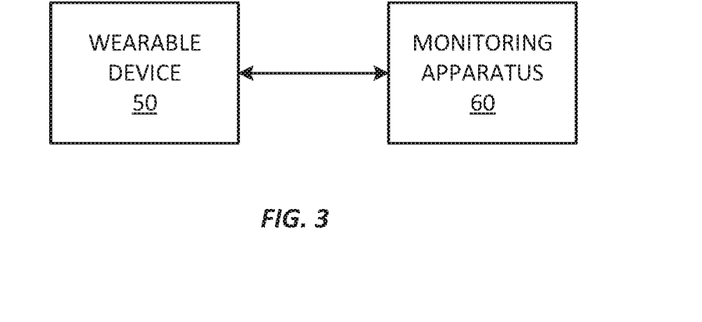
FIG. 3 is a structural schematic diagram of a monitoring system according to an example of the present invention.

FIG. 3 is a structural schematic diagram of a monitoring system according to an example of the present invention. The monitoring system comprises a wearable device 50 and a monitoring apparatus 60 in communicative connection with each other. The wearable device 50 is any one of the wearable devices 50 described above. Parameters associated with regions are preset in the monitoring apparatus 60. In this text, "regions" mean a site to be monitored; the site generally contains electromechanical equipment/robots etc. operating at high speed or other equipment posing a certain danger to entering staff. In the monitoring apparatus 60, regions in a site may be divided into safe regions, regions requiring a warning and highly dangerous regions; the regions may be set by means of transverse and longitudinal position parameters of each region in the site.

The monitoring apparatus 60 receives a sensing signal characterizing a wearer's position and sent by the wearable device 50, and thereby determines whether the position of the wearer is in a safe region, a region requiring a warning, or a highly dangerous region. In the case where the wearable device 50 does not comprise an indication module for issuing warning and other indication signals, the monitoring apparatus 60 may issue a warning signal by itself, e.g. a display or voice indication, etc. A worker in a monitoring room can then immediately issue a human warning to the wearer.

In the case where the wearable device 50 comprises an indication module, the monitoring apparatus 60 sends an indication signal to the wearable device 50, to be shown thereby. For example, when the wearer is in a safe region, the monitoring apparatus 60 sends a signal that the wearer is in a safe region to the wearable device 50; at this time, an optical indication module of the wearable device shows a green colour. When the wearer is in a region requiring a warning, the monitoring apparatus sends a warning signal that the wearer is in a region requiring a warning to the wearable device 50, and the optical indication module disposed on the wearable device 50 shows a yellow colour accordingly. When the wearer is in a highly dangerous region, a warning signal indicating that the wearer is in a highly dangerous region is sent to the wearable device 50, and the optical indication module shows a red colour accordingly. When the wearer receives a warning signal for presence in a highly dangerous region, the signal transceivers simultaneously send the signal to audio indication modules (if the wearable device 50 comprises audio indication modules), so that they issue a warning in audio form that the wearer is in a dangerous region.

Figure 4:
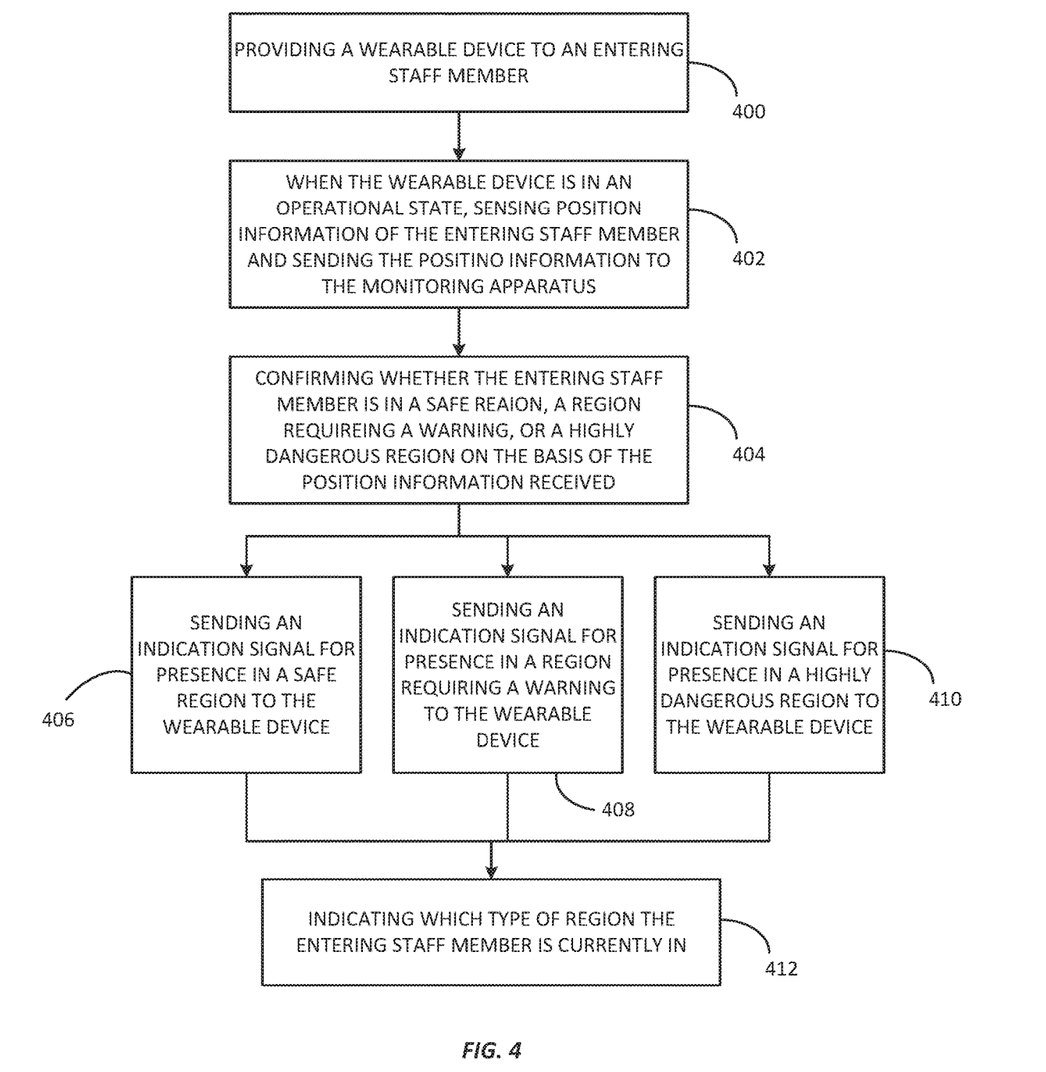
FIG. 4 is a flow chart of a monitoring method for monitoring a site according to an example of the present invention.

According to the present invention, a monitoring method for monitoring a site is also provided. FIG. 4 is a flow chart of the method. According to an example of the present invention, in step 400, a wearable device is provided for an entering staff member to wear; the wearable device is set to comprise a position sensor and a signal transceiver. In step 402, when the entering staff member has put on the wearable device such that the wearable device is in an operational state, the wearable device senses position information of the entering staff member and sends the position information to the monitoring apparatus. In step 404, the monitoring apparatus confirms whether the entering staff member is in a safe region, a region requiring a warning or a highly dangerous region on the basis of the position information received. When it is determined that the entering staff member is in a safe region, step 406 is entered: sending an indication signal for presence in a safe region to the wearable device. When it is determined that the entering staff member is in a region requiring a warning, step 408 is entered: sending an indication signal for presence in a region requiring a warning to the wearable device. When it is determined that the entering staff member is in a highly dangerous region, step 410 is entered: sending an indication signal for presence in a highly dangerous region to the wearable device. In step 412, the wearable device indicates which type of region the entering staff member is currently in, according to the indication signal received.

In the example of FIG. 4, the wearable device may be the wearable device described with reference to FIG. 1 or FIG. 2. Furthermore, the method shown as an example in FIG. 4 may be executed in the monitoring system as shown in FIG. 3.

When the entering staff member wearing the wearable device enters a site to be monitored, the staff member's position in the site can be transmitted in real time to the monitoring apparatus. The monitoring apparatus determines, on the basis of the wearer's position, whether the region in which the wearer is located is a safe region, a region requiring a warning or a highly dangerous region. In the case where the wearer is in a region requiring a warning or a highly dangerous region, a warning is given in optical and/or audio form, and in the case of a high level of danger, a warning is preferably given in both optical form and audio form. Furthermore, although not described in detail above, according to each example of the present invention, when it is determined that the entering staff member (i.e. wearer) has entered a highly dangerous region, the monitoring apparatus may also be configured to control electromechanical equipment or robots operating at high speed in the site, or other equipment posing a threat to entering staff, to stop operating. In other words, the monitoring apparatus may also be configured to adopt certain measures to help keep the entering staff member safe when the entering staff member (i.e. wearer) enters a highly dangerous region; the specific measures may be determined according to the actual environment of the monitored site.

In specific examples described here, the wearable device has been described as being worn on the neck with reference to FIG. 2, but in actual applications, the wearable device could be a pair of spectacles, or could be a wearable device worn on the wrist or ankle. In the case where the wearable device is a pair of spectacles, the first part is for example a spectacles arm while the second part is the other spectacles arm, and a part connected to the spectacles arms corresponds for example to the battery carrier.

Although several examples or embodiments according to the principles of the present invention have been described by means of examples, those skilled in the art could arrange for one or more of these examples to be used in combination with each other, without departing from the principles and spirit of the present invention.

The invention claimed is:

1. A wearable device, comprising:
   a power source;
   a position sensor electrically connected to the power source and configured to determine a position of a wearer of the wearable device and to generate a position signal;
   a signal transceiver electrically connected to the power source and configured to receive the position signal, send the position signal to a monitoring apparatus, and receive an indication signal based on the position signal from the monitoring apparatus; and
   wherein a body of the wearable device comprises a first part and a second part, and a moveable end of the first part and a moveable end of the second part are configured to switch a relative position between a first relative position and a second relative position.

2. The wearable device according to claim 1, wherein switching of the relative position between the first relative position and the second relative position turns the power source on or off.

3. The wearable device according to claim 1, wherein the position sensor includes a first position sensor and a second position sensor, the signal transceiver includes a first signal transceiver and a second signal transceiver, the first position sensor and the first signal transceiver disposed at the first part, and the second position sensor and the second signal transceiver disposed at the second part.

4. The wearable device according to claim 1, wherein the power source is disposed on a power source carrier, the first part being pivot-connected by a non-moveable end thereof to one end of the power source carrier, and the second part being pivot-connected by a non-moveable end thereof to another end of the power source carrier.

5. The wearable device according to claim 3, wherein, in response to the switching of position of the moveable end of the first part between the first relative position and the second relative position, the power source supplies power or stops supplying power to the first signal transceiver and the first position sensor, and, in response to the switching of position of the moveable end of the second part between the first relative position and the second relative position, the power source supplies power or stops supplying power to the second signal transceiver and the second position sensor.

6. The wearable device according to claim 1, further comprising an indication module configured to make a corresponding indication when the signal transceiver receives an indication signal from the monitoring apparatus.

7. The wearable device according to claim 1, wherein a wearing region is any one of a neck, a wrist and a head.

8. A monitoring system, comprising a wearable device and a monitoring apparatus in communicative connection with each other, wherein the wearable device includes
    a power source;
    a position sensor electrically connected to the power source and configured to determine a position of a wearer of the wearable device and to generate a position signal;
    a signal transceiver electrically connected to the power source and configured to receive the position signal, send the position signal to a monitoring apparatus, and receive an indication signal based on the position signal from the monitoring apparatus; and
    wherein a body of the wearable device comprises a first part and a second part, and a moveable end of the first part and a moveable end of the second part are configured to switch a relative position between a first relative position and a second relative position.

9. A monitoring method, comprising:
    receiving, with a monitoring apparatus, a position signal from a wearable device indicating a position of a wearer of the wearable device, wherein the position is determined by the wearable device and wherein a body of the wearable device comprises a first part and a second part, and a moveable end of the first part and a moveable end of the second part are configured to switch a relative position between a first relative position and a second relative position;
    determining, with the monitoring apparatus, a region associated with the position of the wearer based on the position signal; and
    performing, with the monitoring apparatus, a corresponding operation based on the determined region.

10. The monitoring method according to claim 9, wherein performing the corresponding operation includes sending a corresponding indication signal to the wearable device based on the determined region,
    wherein the corresponding indication signal indicates whether the wearer is in at least one selected from a group consisting of a safe region, a region requiring a warning, and a highly dangerous region.

11. The monitoring method according to claim 9, further comprising:
    controlling equipment operating within the determined region based on the determined region.

12. The monitoring method according to claim 9, wherein determining the region associated with the position of the wearer includes determining the region to be at least one selected from a group consisting of a safe region, a region requiring a warning, and a highly dangerous region.

13. The wearable device according to claim 1, further comprising:
    an alarm button electrically connected to the power source and configured to issue a distress signal indicating an emergency situation.

14. The monitoring method according to claim 9, wherein performing the corresponding operation includes
    sending a first corresponding indication signal to the wearable device when the position of the wearer is associated with a first region, and
    sending a second corresponding indication signal to the wearable device when the position of the wearer is associated with a second region,
    wherein the first corresponding indication signal is different from the second corresponding indication signal and the first region is different from the second region.

15. The wearable device according to claim 1, further comprising an optical indication module configured to show a color based on the indication signal received from the monitoring apparatus, wherein the color indicates a region type associated with the position of the wearer.

16. The wearable device according to claim 1, further comprising an indication module configured to indicate a charge level for the power source.

* * * * *